United States Patent [19]

Butterworth et al.

[11] 4,392,861
[45] Jul. 12, 1983

[54] TWO-PLY FIBROUS FACING MATERIAL

[75] Inventors: George A. M. Butterworth, Western Springs; Frank J. Fillwalk, Oak Lawn, both of Ill.

[73] Assignee: Johnson & Johnson Baby Products Company, New Brunswick, N.J.

[21] Appl. No.: 196,809

[22] Filed: Oct. 14, 1980

[51] Int. Cl.³ .................. A61F 13/16; B32B 7/06; B32B 21/02; B32B 21/10
[52] U.S. Cl. .................. 604/366; 428/198; 428/286; 428/290; 428/296; 428/302; 428/913; 604/375; 428/311.9
[58] Field of Search .................. 128/287, 284, 290 W; 428/196, 198, 286, 290, 296, 302, 317, 321, 913; 604/366–367, 375

[56] References Cited

U.S. PATENT DOCUMENTS

| 2,045,095 | 6/1936 | Osborne . |
| 2,414,833 | 1/1947 | Osborne . |
| 2,477,000 | 7/1949 | Osborne . |
| 2,626,214 | 1/1953 | Osborne . |
| 2,708,617 | 5/1955 | Mogat . |
| 2,810,646 | 10/1957 | Wooding et al. . |
| 2,825,282 | 3/1958 | Gergen . |
| 2,899,351 | 8/1959 | Morse . |
| 2,962,414 | 11/1960 | Arledter . |
| 2,962,415 | 11/1960 | Arledter . |
| 2,971,858 | 2/1961 | Di Guilio et al. . |
| 2,971,877 | 2/1961 | Arledter . |
| 2,978,446 | 4/1961 | Battista et al. . |
| 2,999,788 | 9/1961 | Morgan . |
| 3,003,912 | 10/1961 | Harford . |
| 3,013,936 | 12/1961 | Iyeugaa . |
| 3,035,965 | 5/1962 | Mathews . |
| 3,047,455 | 7/1962 | Holmes et al. . |
| 3,047,456 | 7/1962 | Ucci et al. . |
| 3,052,593 | 9/1962 | Battesha . |
| 3,057,772 | 9/1962 | Magill et al. . |
| 3,068,527 | 12/1962 | Morgan . |
| 3,081,519 | 3/1965 | Blades et al. . |
| 3,095,345 | 6/1963 | Jackson et al. . |
| 3,097,991 | 7/1963 | Miller et al. . |
| 3,099,067 | 7/1963 | Merrian . |
| 3,101,294 | 8/1963 | Fridricksen . |
| 3,104,198 | 9/1963 | Brissette . |
| 3,131,088 | 4/1964 | Festag . |
| 3,141,812 | 7/1964 | Marek et al. . |
| 3,141,813 | 7/1964 | Marek et al. . |
| 3,193,447 | 7/1965 | Marek et al. . |

FOREIGN PATENT DOCUMENTS

| 933718 | 9/1973 | Canada . |
| 7313173 | 3/1974 | Netherlands . |
| 697431 | 9/1969 | South Africa . |
| 1102342 | 2/1968 | United Kingdom . |

OTHER PUBLICATIONS

SWP by Crown Zellerback, 1974.
*Textryls Made from DuPont Fibers and Fibrids* by E. I. DuPont DeNemours & Company, (Inc.), 1960.

*Primary Examiner*—James C. Cannon
*Attorney, Agent, or Firm*—Martha A. Michaels

[57] ABSTRACT

A delaminatable two-ply diaper facing material is provided in which an outer ply, or layer, is made of irregularly arranged, intersecting, overlapping, mechanically interengaged, loosely assembled natural wood pulp fibers and an inner ply, or layer, contains similarly disposed natural wood pulp fibers and thermoplastic synthetic wood pulp fibers having a melting point lower than that of other fibers in the layer, the latter being in contact with and heat fused with other fibers to provide structural integrity to the inner layer, with fibers in both layers being bonded to each other by a water soluble adhesive binder.

The material is prepared by bringing together the aforementioned layers, applying heat in the absence of pressure to fuse the thermoplastic synthetic wood pulp fibers in the inner layer to each other and to other fibers, introducing a water soluble adhesive binder into the two layers and then drying and curing the binder.

27 Claims, 5 Drawing Figures

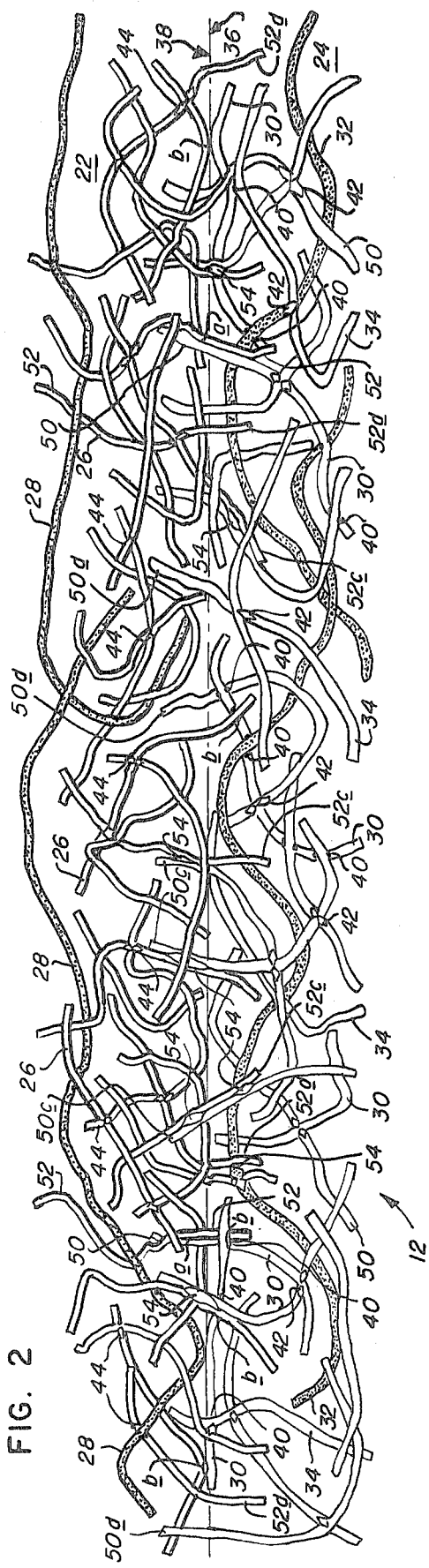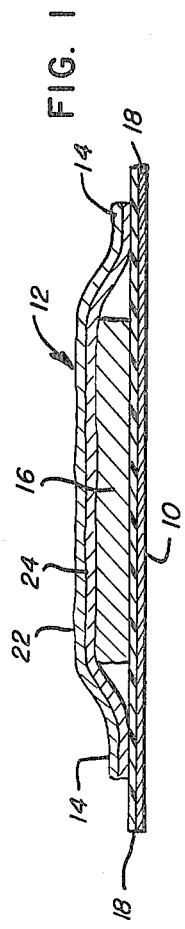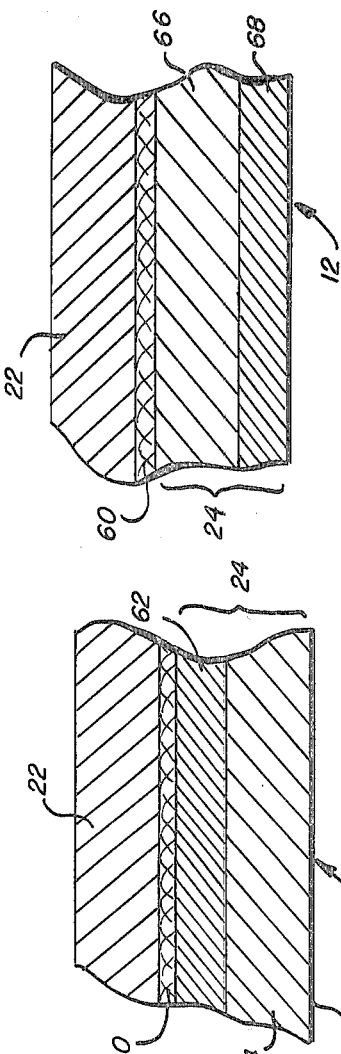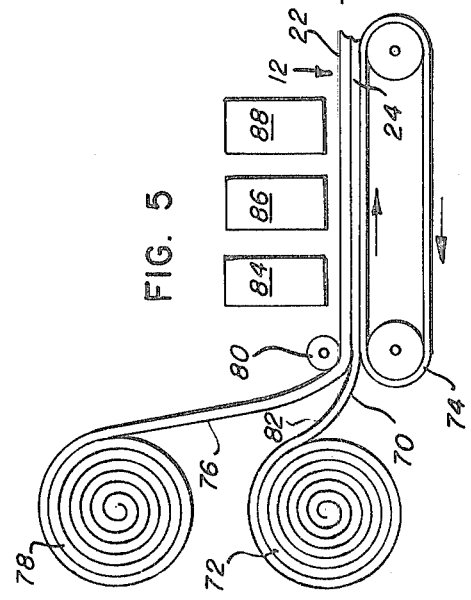

TWO-PLY FIBROUS FACING MATERIAL

This is a continuation-in-part application of application Ser. No. 108,111, filed Dec. 28, 1979, which in turn was a continuation of application Ser. No. 734,206, filed Oct. 20, 1976.

This application relates to a high loft, low density, non-woven, two-ply fibrous material containing synthetic wood pulp fibers as one constituent thereof, more particularly to such a material which can be used as the facing material for an absorbent product such as a diaper, and to a method of producing such a two-ply fibrous material.

BACKGROUND OF THE INVENTION

Synthetic polymeric fibers that have physical and morphological characteristics generally similar to pulp fibers produced from natural woods have been known for approximately 10 years. Examples of such fibers are the synthetic wood pulp fibers formed of polyethylene that are sold by Crown Zellerbach under the trademark SWP.

Various methods of making synthetic wood pulp fibers are known, including (1) solution polymerization accompanied by stirring, (2) dissolving a preformed polymer and subjecting the solution of an anti-solvent, or (3) forming the polymer at the interface between liquid layers, with localized stirring provided to pull the polymers thus formed into fibrillated forms. Examples of methods of producing synthetic wood pulp fibers are disclosed in U.S. Pat. Nos. 3,560,318; 3,081,519; 3,003,912; 3,068,527; and 3,290,207; South African Pat. No. 697,431; and United Kingdom Pat. No. 1,102,342; and Netherlands Patent Application A132/48–7313173.

As used in this specification and the appended claims, the term "synthetic wood pulp fibers" means synthetic, water dispersible, thermoplastic, elongated, supple, randomly bent, polymeric fibers or fibrils generally similar in length and denier to conventional wood pulp fibers produced from naturally occurring woods. Each such "synthetic wood pulp fiber" is of irregular cross sectional shape measured at any given point along its length, and in addition is nonuniform in cross section along its length. The predominant shape of the fibers is usually rather ribbon-like.

Though synthetic wood pulp fibers are similar in length and denier to conventional wood pulp fibers, their uniformity is better and their size and shape consistency greater. Whereas, conventional wood pulp fibers have a length which varies from 0.5 mm to 5.0 mm and a coarseness of between ten and twenty decigrex synthetic wood pulp fibers have a length of from one to four millimeters and a coarseness of between three and ten decigrex (as disclosed, for example, in the section headed "Fiber Dimensions" in the Sept. 1974 publication by Crown Zellerbach entitled SWP.

Comparing some of the other properties of synthetic wood pulp fibers with conventional wood pulp, a conventional wood pulp fiber has from 1 to 5 times the breaking stress of synthetic wood pulp; whereas, the synthetic wood pulp fiber elongates at rupture 3 to 5 times as much as a conventional wood pulp fiber, hence, the overall toughness of a synthetic wood pulp fiber is similar to or even greater than that of a conventional wood pulp fiber (as disclosed, for example, in the section headed "Single Fiber Stress-Strain Behavior" in the September, 1974 publication by Crown Zellerbach entitled SWP).

The present invention utilizes synthetic wood pulp fibers in a high loft, low density, nonwoven fibrous material such as an air-laid web or fabric. Nonwoven materials are structures which consist of an assemblage or web of irregularly arranged fibers, joined randomly or more or less systematically by mechanical, chemical or other means. These materials are well known in the art, having gained considerable prominence within the last twenty years or so in the consumer market, the industrial commercial market and the hospital field. For example, nonwoven materials are becoming increasingly important in the textile and related fields, one reason being because of their low cost of manufacture for a given coverage as compared to the cost of more conventional textile fabrics made by weaving, knitting or felting. Typical of their use is the production of hospital caps, dental bibs, eye pads, dress shields, shoe liners, shoulder pads, skirts, hand towels, handkerchiefs, tapes, bags, table napkins, curtains, draperies, and the like. Generally speaking, nonwoven materials are available today in a wide range of fabric weights of from as little as about 100 grains/sq. yd. to as much as about 4,000 grains/sq. yd., or even higher.

A number of processes and types of apparatus are known for producing nonwoven materials. These include (1) mechanical techniques (e.g., carding or garnetting), (2) wet-laying techniques (e.g., inclined wire paper apparatus, cylinder paper apparatus, etc.), and (3) air-laying techniques. The high loft, low density, nonwoven materials such as webs or fabrics to which this invention relates may suitably be produced, in the manner to be explained in detail below, from layers of material manufactured by well-known air-laying processes.

The product of this invention utilizes synthetic wood pulp fibers in a novel high loft, low density, nonwoven, two-ply fibrous material that is useful as one component of an infant's disposable diaper. The material is also useful in other absorbent products such as sanitary napkins, surgical bandages, disposable bed pads, and the like.

Disposable diapers are typically constructed of three components. Two of these components are a backing sheet, formed for example of a polyethylene film, and a facing layer that has its peripheral portions attached to the backing sheet. The facing layer is positioned next to the infant when the diaper is in use. The third component, which is contained between the first two components just described, is a cellulosic batt, formed for example of wood pulp fluff or cotton linters.

The facing layer of a known disposable diaper is typically a one-ply layer formed of rayon and wood pulp fibers, with a surfactant and a water repellent binder, such as an acrylic polymer, distributed through the layer of fibers in a specified manner. A balance of wettability is achieved in this way in order to control the flow of liquid through the facing layer in a desired manner. The facing layer is (1) not passing from outside the diaper through the layer into the cellulosic batt located in the mid-portion of the diaper, but (2) more water repellent than the cellulosic batt, so that urine that passes through the layer will remain in the batt rather than passing back out of the diaper through the facing layer.

SUMMARY OF THE INVENTION

The present invention provides a facing layer that is a two-ply structure with definite advantages in the manner of disposal of the used diaper because of the different characteristics of the two plies. The outer ply of the facing layer, which becomes most soiled with solid waste matter in use, is disposable in a flush toilet. The inner ply, which becomes soiled with solid matter only to a limited extent if at all during use, provides structural strength for the assembled two-ply layer both during and after use, and is separately disposable after use, together with the backing sheet and the enclosed cellulosic batt, in a covered container from which it can be removed and discarded later.

The two-ply facing material of this invention is constructed in such a manner that when it is incorporated in a diaper (1) normal handling of the dry diaper as a whole can be carried out without damage to the facing material, (2) the outer ply of the facing layer has sufficient mechanical integrity that it will not disintegrate when the facing layer is immersed for a short time in water and the outer ply is pulled apart from the inner ply, and (3) when the assemblage deposited in a flush toilet, the fibrous mass will disintegrate into a multiplicity of separate, individual fibers and small clumps of fibers which can pass through the sewage disposal system without causing clogging.

The two-ply facing material of this invention comprises a first outer layer of irregularly arranged, intersecting, overlapping, mechanically interengaged, loosely assembled natural wood pulp fibers defining interstices therebetween, and a second inner layer of similarly disposed fibers including intermixed natural wood pulp fibers and synthetic wood pulp fibers. The synthetic wood pulp fibers in the inner layer, which have a melting point lower than the melting point of the other fibers in the facing material, are in contact with and heat fused with other fibers in the layer to form a fiber structure of sufficient wet strength and integrity to be self-supporting in both dry and wet condition without any additional binder.

Fibers in each of the two layers are also bonded with one another and with fibers in the other layer by a water soluble adhesive binder to provide the desired mechanical integrity for normal handling of the dry material as a whole. In addition, the bonding of fibers of the outer layer to each other by the introduction of adhesive binder avoids disintegration of the outer layer when the bond between the two layers (1) is first weakened by immersion in the water of a flush toilet for a limited time to dissolve out only a portion of the water soluble binder, and (2) is then ruptured by pulling the two layers apart. Following the rupture of the bond between the layers, the outer fibrous layer can be deposited in the flush toilet, where the remainder of the water soluble adhesive binder will be dissolved out and the outer layer will disintegrate into separate, individual fibers and small clumps of fibers. The water soluble adhesive binder employed should be substantially less soluble in body fluids such as urine than in water, and preferably substantially insoluble in such fluids.

Synthetic wood pulp fibers in the inner layer of the two-ply facing material of this invention are present at the boundary surface of the inner layer adjacent the interface between the two layers in a quantity sufficient to occupy no more than about 6 percent of the area occupied by exposed fiber segments contained in the inner layer at that boundary surface. In addition, fiber segments extending from either the inner or the outer layer across the interface between them and into the interstices between the fibers of the other layer are substantially limited to outer end portions of such fibers. These two features permit a firm bond between the inner and outer layers of the two-ply product of this invention due to the presence of the water soluble adhesive binder, and also due to the limited heat fusion of synthetic wood pulp fibers in the inner layer with other fibers in both the inner layer and the boundary surface portions of the outer layer adjacent the interface between the two layers, without making that bond so strong that it will interfere with delamination of the two layers when a substantial portion of the adhesive binder is removed and the two layers are pulled apart in the manner described above.

The bond between the two plies is sufficiently strong, and yet permits easy delamination of the facing layer as described, if the defined percentage of synthetic wood pulp fibers is no more than about 4 percent. Delamination is still easier if the percentage is no more than about 2 percent.

An improved product is obtained if the outer layer is substantially free of synthetic wood pulp fibers. Further improvement in delamination without undue decrease in the structural strength of the inner ply of the facing material is obtained if the concentration of synthetic wood pulp fibers in the inner layer is greatest in a region spaced from the boundary surface of the inner layer that is adjacent the interface between the two plies. This effect is made even greater if the boundary surface of the inner layer adjacent the interface is substantially free of synthetic wood pulp fibers.

A satisfactory product is obtained if the inner layer contains no more than about 30 percent by weight of synthetic wood pulp fibers. The product is further improved if that percentage is no more than about 20 percent, and it is preferred that it be no more than about 10 percent. If desired, for added fabric strength, the inner layer may contain some textile length fibers intermixed with the natural wood pulp fibers and synthetic wood pulp fibers. For the same purpose of added strength of the fibrous material, the outer layer may contain some textile length fibers in addition to natural wood pulp fibers.

In the method of this invention, the first outer layer and second inner layer of fibers are brought together, and heat in the absence of pressure is applied to the two fibrous layers to produce the heat fusion and bonding of fibers described above so as to form a self-supporting fibrous structure in the second layer. A water soluble adhesive binder is then introduced into the two fibrous layers and at the interface between them, and the binder is dried and cured to produce the two-ply facing material of this invention.

Surprisingly, the minor proportions of synthetic wood pulp fibers referred to for inclusion in the inner layer of the facing material of this invention as a whole produce a good degree of mechanical integrity in the inner layer. It is perhaps still more surprising that the very minor proportions of synthetic wood pulp fibers present in the inner layer at the interface between the outer and inner layers produce a reliable bond between the two plies of the facing material when reinforced with added adhesive binder (but without the lamination pressure indicated in the disclosure in the section headed "Applications—Nonwovens and Laminates" in the September 1974 publication by Crown Zellerbach entitled SWP), and at the same time will permit substantially all the fibers of the outer layer to be stripped off the inner layer as a group when it is desired to dispose of them in a flush toilet in the manner described above.

Thus, the practice of this invention produces a very useful product through utilization in a novel manner of quite small quantities of synthetic wood pulp fibers.

BRIEF DESCRIPTION OF THE DRAWINGS

The invention will now be described with reference to the accompanying drawings in which:

FIG. 1 is a reduced diagrammatic cross sectional view of an infant's disposable diaper with the two-ply facing material of this invention incorporated therein;

FIG. 2 is an enlarged, fragmentary diagrammatic representation in cross section of the two-ply facing material for a disposable diaper that is the product of this invention;

FIGS. 3 and 4 are enlarged, fragmentary diagrammatic cross sectional views of two embodiments of the fibrous material of this invention; and FIG. 5 is a diagrammatic side elevational view of one form of apparatus for producing the fibrous material of this invention.

DETAILED DESCRIPTION OF THIS INVENTION

End Use of Two-Ply Facing Material of This Invention

FIG. 1 gives a reduced diagrammatic cross sectional view of an infant's disposable diaper with the two-ply facing material of this invention incorporated therein. Backing sheet 10 is formed of a polyethylene sheet. Facing material 12 has its edge portions 14 attached to backing sheet 10, with cellulosic batt 16 being formed of wood pulp fluff contained between sheet 10 and facing material 12.

Edge portions 18 of backing sheet 10 may be secured to other portions of the diaper to hold it in place on the infant. Outer layer 22 of facing material 12 lies next to the infant's body when the diaper is in place. Inner layer 24, which contains synthetic wood pulp fibers, provides structural strength to the assembled two-ply facing layer 12.

General Structure of Facing Material of This Invention

FIG. 2 is an enlarged, fragmentary, diagrammatic representation in cross section of two-ply facing material 12 of FIG. 1.

The fiber structure shown in the lower half of FIG. 2, which constitutes ply 24, has sufficient wet strength and integrity to be self-supporting in both dry and wet conditions without any additional binder. The fiber structure in the upper half of FIG. 2, which constitutes outer layer 22 of two-ply facing material 12, is bonded to layer 24 with sufficient strength to avoid damage to the bond between the layers during normal handling in the dry state, but can be removed from inner layer 24 in the manner referred to above, to be discarded in a flush toilet.

Outer layer 22 is formed of irregularly arranged, intersecting, overlapping, mechanically interengaged, loosely assembled fibers which define interstices therebetween. The term "mechanically interengaged" is used in this specification and claims to refer to fibers (usually randomly bent) that are interlocked or interentangled with other fibers to provide a degree of structural integrity whether or not binder is present in the layer of fibers.

In the embodiment shown, layer 22 contains two types of fibers. Fibers 26 are natural wood pulp fibers. Fibers 28 (stippled in the drawing) are longer textile type fibers, which are included to provide additional structural strength for layer 22. These textile length fibers may be natural fibers, artificial fibers, or synthetic fibers, so long as they are compatible with natural wood pulp fibers 26 and do not interfere with a soft, fluffy, external boundary surface for outer layer 22.

The fibers of inner layer 24 are in general disposed similarly to the fibers of outer layer 22. The fibers specifically indicated by the designator numeral 30 in inner layer 24 of FIG. 2 are synthetic wood pulp fibers. Synthetic wood pulp fibers 30 have a melting point lower, preferably by about 10° to 20° C., than the melting point of the other fibers in facing material 12. Fibers 32, stippled in the drawing, are textile length fibers included to give the inner layer greater structural strength. All the other fibers of layer 24, some of which are designated as fibers 34 are natural wood pulp fibers.

In FIG. 2, for illustrative purposes, synthetic wood pulp fibers 30 are represented in their original configurations (i.e., as they look prior to heat treatment). The heat treatment may alter the configurations, either slightly or substantially, depending on the severity of the heat treatment step. However, even in substantially altered configurations, the synthetic wood pulp fibers still provide effective interfiber bonding.

Fibers 26 and 29 of outer fibrous layer 22 have a great multiplicity of contact points throughout the layer. Fibers 20, 32 and 34 of inner fibrous layer 24 likewise have a great multiplicity of contact points with other fibers throughout that layer.

In the embodiment shown, synthetic wood pulp fibers 30 represent about 20 percent of the total weight of fibers in inner fibrous layer 24. However, synthetic wood pulp fibers 30 are present at boundary surface 36 of inner layer 24 at the interface with boundary surface 38 of outer layer 22 in a quantity sufficient to occupy only about 6 percent of the area occupied by exposed fiber segments contained in layer 24 at boundary surface 36. The structural strength of inner layer 24 is increased when the total layer is about 30 percent by weight of synthetic wood pulp fibers, but the 20 percent figure produces a softer product with sufficient strength in most cases, and it is preferred that the figure be no more than about 10 percent for adequate strength and improved softness. If the percentage of synthetic wood pulp fiber segments exposed at boundary surface 36 is reduced to 4 percent, delamination of layers 22 and 24 in the manner described above is made easier, and with that figure at about 2 percent delamination is made still easier.

A satisfactory two-ply nonwoven facing material may be produced according to this invention weighing between 100 grains/sq. yd. and about 1200 grains/sq. yd., or even higher. If desired, outer layer 22 and inner layer 24 may be formed by means of an air deposition process.

Bonding of Fibers Within Inner and Outer Layers

The structural strength of inner fibrous layer 24 is derived from two types of bonds between various fibers of that layer. Synthetic wood pulp fibers 30 provide fusion bonding—at contact zones designated by dark lines in FIG. 2, a representative number of which are identified by designator numerals 40—with other fibers with which they are mechanically interengaged. These fusion bonds between synthetic wood pulp fibers 30 and other fibers of layer 24 form a fiber structure of sufficient wet strength and integrity to be self-supporting in both dry and wet condition without any additional binder.

A second type of bonding is provided in inner fibrous layer 24 by globules of a water soluble adhesive binder that bond various mechanically interengaged fibers 30, 32 and 34 to provide additional structural integrity. A representative number of such globules of adhesive binder is marked with designator numeral 42 in FIG. 2. The water soluble binder, for reasons to be explained below, should be substantially less soluble in body fluids such as urine than in water, and preferably substantially insoluble in such fluids.

Mechanically interenegaged fibers 26 and 28 of outer fibrous layer 22 are likewise bonded together at various contact points by globules of the same type of water soluble adhesive binder, which in this case constitute the only means bonding the fibers of the layer to each other. A representative number of such globules of binder in the outer layer is marked in FIG. 2 with designator numeral 44.

The bonding of mechanically interengaged fibers in inner and outer fibrous layers 24 and 22 by globules of water soluble adhesive binder 42 and 44, respectively, provides sufficient mechanical integrity throughout two-ply facing material 12 to allow normal handling of the dry material as a whole, either as a separate facing material or as a layer 12 incorporated in a disposable diaper such as shown in FIG. 1.

Bonding Between Inner and Outer Layers

There are three types of bonds between outer fibrous layer 22 and inner fibrous layer 24 that make up two-ply facing material 12. Two of these types of bonds are heat fusion bonds between synthetic wood pulp fibers 30 in inner fibrous layer 24 and fiber segments (in the embodiment shown limited to segments of natural wood pulp fibers 26) in outer fibrous layer 22. The third type of bond is produced through use of water soluble adhesive binder.

As is seen in FIG. 2, the greater part of the fibrous masses that comprise inner fibrous layer 24 and outer fibrous layer 22 lie within the interior of the respective fiber structures as a whole. In fact, in the case of a number of the fibers, the individual fiber lies within the interior of the fiber structure for the entire fiber length. However, a number of fibers of layer 24 have free fiber ends 50 extending outwardly from at least one boundary surface of the layer. In FIG. 2, some of free fiber ends 50 extending upwardly from effective upper boundary surface 36 of layer 24 help to bond fibrous layers 22 and 24 together. Outer fibrous layer 22 likewise has free fiber ends 52 extending outwardly from the layer. In FIG. 2, some of free fiber ends 52 extending downwardly from the plane of lower boundary surface 38 of layer 22 help to bond fibrous layers 22 and 24 together.

As is illustrated in diagrammatic fashion in FIG. 2, fiber end portions 50 and 52 that extend outwardly beyond their respective boundary surfaces 36 and 38 have a considerable degree of contact with fiber segments of the other layer. FIG. 2 is not intended to suggest that the precise types of contact and bonding shown there are necessarily identifiable in the product of this invention, but it is intended to suggest some considerable degree of contact between the fibers in question.

As shown, it is believed that some exposed fiber end portions 50 of synthetic wood pulp fibers 30 that are mechanically engaged with other fibers of inner fibrous layer 24 are in contact with outwardly extending end portions 52 of fibers 26 in outer fibrous layer 22. Contact of this type is indicated by the letter "a" in FIG. 2 in the left-hand and right-hand portions of the figure.

At contact zones "a", segments of synthetic wood pulp fibers 30 of inner fibrous layer 24 are heat fused with segments of fibers 26 of outer fibrous layer 22. This interfiber contact and fusion is believed to provide a minor portion of the bond between inner layer 24 and outer layer 22 when facing material 12 is in the dry state.

Another type of fusion bonding of still less importance, but which adds somewhat to the strength of the bond between fibrous layers 24 and 22, is provided at the essentially two-dimensional contact of certain of the fiber segments that lie parallel or in skew relationship to each other adjacent respective boundary surfaces 36 and 38 at the interface between the two fibrous layers. Examples of this supplementary interfiber contact and fusion are shown at "b" at the extreme left-hand and right-hand ends of FIG. 2.

The third type of bonding between inner fibrous layer 24 and outer fibrous layer 22 is supplied by globules of water soluble adhesive binder 54 that bind outwardly extending fiber end portions 50c and 52c with fiber segments of the opposing layer. Examples of adhesive bonds 54 are shown in various locations above and below interface 36/38 across the drawing of FIG. 2. The interfiber bonding produced by binder globules 54 is believed to provide the major portion of the strength of the bond between inner fibrous layer 24 and outer fibrous layer 22 when two-ply facing material 12 is in the dry state. The adhesive binder former globules 54 should have the same relative solubility in water and in body fluids such as urine as the binder forming globules 42 and 44 discussed above.

Some exposed fiber end portions 50d protruding from inner fibrous layer 24 across interface 36/38, and some exposed fiber end portion 52d protruding in the opposite direction across the interface, fail to make contact with any fibers in the opposing fibrous layers. Examples of such situations are shown at various locations across FIG. 2.

The combined effect of the fusion bonding at contact zones "a" and "b" and the adhesive bonding from globules 54 provides a bond of sufficient strength that two-ply facing material 12 can be subjected to normal handling in the dry state as a whole, either alone or incorporated in the disposable diaper of FIG. 1, without damage to the material. However, the fusion bonding at contact zones "a" and "b" is not sufficient alone to prevent stripping of substantially all the fibers of outer fibrous layer 22 from inner fibrous layer 24 when the bonding force of adhesive binder globules 54 acting on the two fibrous layers is diminished as will be described below.

The relatively weak character of the bond between fibrous layers 24 and 22—in comparison to the structural integrity of the remainder of the facing material—that results from the heat fusion of synthetic wood pulp fibers 30 alone, and unreinforced by the full additional bonding force from adhesive binder globules 54, is due to three factors. First, synthetic wood pulp fibers 30 are present at interface 36/38 in a quantity sufficient to occupy no more than about 6 percent of the area occupied by exposed fiber segments of all kinds of contained in inner fibrous layer 24 at boundary surface 36. Second, the essentially two-dimensional fusion bonding at contact zones "b" is not a strong bond. Third, no synthetic wood pulp fibers extend across interface 36/38 with large fractions of their lengths being mechanically interengaged with fibers on both sides of the interface. In other words, fiber segments extending either from inner fibrous layer 24 or from outer fibrous layer 22 across interface 36/38 between the two layers and into the interstices between the fibers of the other layer are substantially limited to the outer end portions only of such fibers, which segments constitute only a relatively small portion of each synthetic wood pulp fiber 30, and are in addition likely to be fairly straight in form rather than bent in such a manner as to facilitate the mechanical interengagement of fibers that is typical of the main body of said fibrous layer.

Stripping of Outer Layers From Inner Layers After Use

As indicated above, because of the structure of two-ply facing material 12 thus far described, a diaper incorporating this facing material can be subjected to normal handling in the dry state without damage to the facing material. In addition, when adhesive binder 54 distributed throughout facing material 12 is removed in two stages, the described structure of the facing material makes possible the substantial stripping of outer fibrous layer 22 from inner fibrous layer 24, and thus from the rest of the diaper.

In the first stage of removal of adhesive binder 54 from facing material 12, some but not all of the binder is removed by immersing the used diaper, together with any fecal matter that has been deposited on outer layer 22, in the water contained in the bowl of a flush toilet. If the soiled diaper is swirled around in the water briefly, the solid waste matter will be largely rinsed off the diaper and a portion of water soluble binder 54 will be dissolved out of facing material 12. This submersion in water should not be continued too long, since it is not desired to remove all of water soluble adhesive binder 54 at this stage.

With a portion of binder 54 thus removed from the vicinity of interface 36/38, the essentially weak bond between fibrous layers 24 and 22 produced solely by the heat fusion bonding described above is only partially reinforced by the remaining quantity of adhesive binder. At the same time, the inherent web strength due to the original mechanical interengagement of whole fibers in fibrous outer layer 22 is still somewhat reinforced by the remaining portion of adhesive binder 44 distributed throughout the layer.

The greater strength of the mechanical interengagement of fibers in layer 22—reinforced as just indicated by the remaining portions of adhesive binder 44—compared to the weakened bond between the layers 22 and 24 at interface 36/38 means that after the initial immersion in the toilet bowl, fibrous outer layer 22 will have sufficient mechanical integrity to avoid disintegration of layer 22 when it is pulled apart from inner fibrous layer 24 to rupture the bond between the two layers. At this juncture, inner fibrous layer 24 remains a self-supporting web by reason of the heat fusion bonding at contact zones 40, as supplemented by the remaining portion of adhesive binder globules 42. Inner layer 24 can thus be discarded, along with backing sheet 10 and cellulosic batt 16 of the disposable diaper, by being temporarily stored in a covered container from which it can be removed and discarded later.

Outer fibrous layer 22 as stripped from inner layer 24 in the manner described comprises a separate assemblage of substantially all the natural wood pulp fibers 26 and textile fibers 28 that were originally in outer layer 22. This assemblage of fibers, together with any residue of solid matter not rinsed away by the swirling action in the toilet bowl, can be flushed down the toilet into the residential water disposal system. There, after the remaining portion of water soluble binder 44 and any portion of binder 54 still adhering to the fibers is dissolved out of the fibrous mass, the assemblage of fibers will disintegrate into a multiplicity of separate individual fibers and small clumps of fibers that will not clog the toilet or the sewage disposal system.

Various Embodiments of the Facing Material of This Invention

To reduce resistance of the disintegration into separate fibers and small clumps of fibers just described, it is preferred that outer fibrous layer 22 of the two-ply facing material of this invention be substantially free of synthetic wood pulp fibers, so that no heat fusion bonding will be present in that layer. Thus, outer fibrous layers 22 in the embodiments represented diagrammatically in FIGS. 3 and 4 contain only natural wood pulp fibers and no synthetic wood pulp fibers.

Regions 60 in two-ply facing materials 12 in FIGS. 3 and 4 represent the regions in the vicinity of the interface between layers 22 and 24, where there is some degree of heat fusion bonding and adhesive bonding between the fibers of the two layers. (See, for example, interface 36/38 in FIG. 2.) When the mechanical interengagement and interentanglement of fibers originally present in outer fibrous layer 22 is fairly extensive, the concentration of synthetic wood pulp fibers in fibrous inner layer 24 may, if desired, be greatest in region 62 immediately adjacent region 60 (FIG. 3), although the quantity of synthetic wood pulp fibers present immediately adjacent the interface between the two layers should in no event be more than a quantity sufficient to occupy at the most about 6 percent of the area occupied by exposed fiber segments contained in inner layer 24 at the interface. In the embodiment shown in FIG. 3, region 64 of inner fibrous layer 24 adjacent external boundary 65 of the layer is substantially free of synthetic wood pulp fibers, and the fibers of that type in region 62 provide layer 24 with the needed wet strength.

To provide fabric strength for inner fibrous layer 24 without strengthening the bond that exists independently of adhesive binder 54 at the interface between layers 22 and 24, it is desirable that the concentration of synthetic wood pulp fibers in inner layer 24 be greatest in a region spaced from the interface. In fact, if for some reason the degree of fiber interengagement and interentanglement present in outer fibrous layer 22 before the introduction of adhesive binder 44 is somewhat lower than is usual in fibrous webs of this type, it is preferred that the boundary surface of inner fibrous layer 24 adjacent the interface between the layers be substantially free of synthetic wood pulp fibers. Thus, in the embodiment of FIG. 4, region 66 immediately adjacent the interface between layers 22 and 24 is substantially free of synthetic wood pulp fibers, and the greatest concentration of such fibers is in region 68 spaced from the interface.

It should be understood that while for purposes of clarity, FIGS. 3 and 4 show fibrous layers adjoining each other within layer 24 at sharply defined interfaces, in most cases there will be a more or less gradual transition from one region to another within that layer, with fibers intermingled as described above, as each region merges into the adjoining region.

The desired balance of wettability in facing layer 12, to permit the passage of liquid into cellulosic batt 16 located in the midportion of the diaper of FIG. 1 while deterring the liquid from passing back out of the batt in the other direction, can be achieved, if desired, by appropriate blending of wettable and nonwettable synthetic wood pulp fibers in inner fibrous layer 24. Nonwettable synthetic wood pulp fibers are formed of hydrophobic polymers, and in commercial form should be free of any surfactant film or water soluble finish on the external surface of the fibers.

The Water Soluble Adhesive Binder

For reasons already pointed out above, the adhesive binder forming globules 42 and 44 in the two fibrous layers 24 and 22, respectively, and globules 54 at interface 36/38 must be water soluble. As used in this specification and claims, the term "water soluble adhesive binder" means a binder that loses its integrity in contact with water, and includes binders that are readily dispersible in water as well as those which form true solutions in water.

The strength of the bonds provided by binder globules 42, 44 and 54 must not be reduced prematurely, or outer fibrous layer 22 may be stripped off inner layer 24 or may begin to disintegrate into individual fibers or small clumps of fibers before this is desired. Hence, the water soluble adhesive binder employed at junctions 42, 44 and 54 should be substantially less soluble in body fluids such as urine than in water, and preferably substantially insoluble in such fluids. Illustrative of such binders are cationic polyurethanes derived from the amine-capped condensation products of a polyisocyanate with a polyol and a tertiary amine that are further reacted with a dihaloalkene. Preferably, these binders are biodegradable.

Other suitable water-dispersible binders are latices of a polyethylacrylate copolymer containing small amounts of acrylonitrile and a cross-linking monomer. One such latex is commercially available under the designation HYCAR 2600 X 120. This latex is self cross-linking, and its extent of cross-linking can be controlled by the severity of the curing conditions to which it is exposed. It is preferred to utilize mild curing conditions and to obtain only limited cross-linking.

The bonding agent should preferably be of the low viscosity type with a viscosity less than 5 centipoises. To avoid excessive water repellency, a surfactant, preferably an anionic surfactant, is included in the binder suspension. A typical surfactant which has been found to be suitable is the ionic sulfonated alkyl ester sold under the trademark Triton GR-5.

Method of This Invention

FIG. 5 gives a diagrammatic showing of one form of apparatus which can be used in the manufacture of the two-ply facing material of this invention.

A web of fibers 70 is fed from supply roll 72 onto the upper reach of endless belt 74, where it will be transformed into inner fibrous layer 24 of facing material 12 after it has passed through the apparatus shown. Fibrous web 70 may comprise a blend of natural wood pulp fibers, synthetic wood pulp fibers, and if desired for greater strength, textile length fibers, which blend may be uniform or non-uniform throughout its thickness. If fibrous web 70 comprises a blend of fibers in which different proportions of synthetic wood pulp fibers are present in successive regions passing through the layer in a direction perpendicular to its median plane, the web may be manufactured by use of the web forming method disclosed in commonly assigned U.S. Pat. No. 3,768,118 to Ruffo, et al.

Fibrous layer 70 comprises a layer of irregularly arranged, intersecting, overlapping, mechanically interengaged, loosely assembled, intermixed natural wood pulp fibers and synthetic wood pulp fibers defining interstices therebetween. Fibrous web 76, fed from supply roll 78 around idler roll 80 and onto fibrous web 70, comprises a layer of natural wood pulp fibers that are disposed similarly to the fibers of web 70.

The synthetic wood pulp fibers in web 70 are present at the upper boundary surface 82 of the web in a quantity sufficient to occupy no more than about 6 percent by weight of the area occupied by exposed fiber segments contained in the web at that boundary. The synthetic wood pulp fibers have a melting point lower, preferably by at least about 10° to 20° C., than the melting point of the other fibers of both webs 70 and 76.

At idler roll 80, fibrous web 76 is brought together with web 70 supported by endless belt 74, to travel from left to right through the apparatus of FIG. 5 and be bonded to the lower fibrous layer to form outer layer 22 of the two-ply facing material of this invention. Fibrous web 76 contains natural wood pulp fibers and, if desired for greater strength, textile length fibers.

Since endless belt 74 and its associated machinery will inevitably have some degree of fibration due to the moving parts of the apparatus, there will be some relative movement between fibrous webs 70 and 76 as they are brought together and moved on through the apparatus. This will tend to cause at least some of the fiber end portions extending outwardly from their respective fibrous webs across the interface between the two webs to insert themselves within the interstices between the fibers of the opposite layer. As this happens, some fiber segments of each layer come into contact with fiber segments in the other layer to produce the interfiber contact discussed above in connection with the description of the types of bonding produced between the inner and outer layers of two-ply facing material 12.

As fibrous webs 70 and 76 are thus brought together and moved along endless belt 74, they passed under infrared heater 84 shown diagrammatically in FIG. 5, to raise the temperature of the fibers in fibrous layer 24 above the melting point of the synthetic wood pulp fibers. This application of heat will fuse at least some of the synthetic wood pulp fibers in fibrous web 70 to each other and to some of the other fibers within the web, to form a self-supporting fiber structure such as described above in connection with fibrous layer 24 in FIG. 2. If desired, heating means 84 may be a radiant heater, air drier, or other suitable means.

As the heat treated webs continue to the right in FIG. 5, they pass beneath spray binding means 86 shown diagrammatically in FIG. 5. Spray binder 86 introduces a water soluble adhesive binder into the two fibrous webs, including the interface between them.

As fibrous webs 70 and 76 continue to the right in FIG. 5, the adhesive binder added at spray binding means 86 is heated by drying means 88 shown diagrammatically in FIG. 5 and thereby dried and cured to the level required by the drying step. At least a portion of the heating should preferably be effected by use of heating means that applies heat to the midportions of the assembled fibrous layers, in order to avoid undue migration of binder to the external surfaces of the resulting facing material.

Webs 70 and 76 are thus transformed into inner layer 24 and outer layer 22, respectively, of two-ply facing material 12 described above in connection with FIG. 2. The facing material thus produced may be used, as pointed out above, as one component of a disposable infant's diaper, a sanitary napkin, an adhesive bandage, disposable bed pad, or other absorbent product.

The above detailed description of this invention has been given for clarity of understanding only. No unnecessary limitations should be understood therefrom, as modifications will be obvious to those skilled in the art.

We claim:

1. A high loft, low density, nonwoven, fibrous two-ply facing material for an absorbent product such as a diaper which comprises a first outer layer of irregularly arranged intersecting, overlapping, mechanically interengaged, loosely assembled natural wood pulp fibers defining interstices therebetween, and a second inner layer of similarly disposed fibers in contact with said outer layer at an interface between said two layers, said inner layer including intermixed natural wood pulp fibers and thermoplastic synthetic wood pulp fibers, said synthetic wood pulp fibers having a length and denier generally similar to natural wood pulp fibers, said inner layer containing generally in the range of about 10 percent to about 30 percent by weight of synthetic wood pulp fibers and said synthetic wood pulp fibers being present at the boundary surface of said inner layer adjacent said interface in a quantity sufficient to occupy no more than about 6 percent of the area occupied by exposed fiber segments contained in said inner layer at its said boundary surface, said synthetic wood pulp fibers having a melting point lower than the melting point, or degradation temperature, of the other fibers in said two-ply facing material, fiber segments extending from either of said fibrous layers across said interface between the two layers and into the interstices between the fibers of the other layer being substantially limited to outer end portions of such fibers, said synthetic wood pulp fibers in said inner layer having been heat fused in the absence of pressure in contact with other fibers in said layer to form a fiber structure of sufficient wet strength and integrity to be self-supporting in both dry and wet condition without any additional binder, the fibers in each of said two layers being bonded with one another and with fibers in the other layer by a water soluble adhesive binder to provide sufficient mechanical integrity throughout said two-ply facing material to allow normal handling of the dry material as a whole, and to help provide, together with the already existing mechanical interengagement of whole fibers in said outer layer, sufficient mechanical integrity in said outer layer to avoid disintegration of said outer layer when the bond between said two layers is weakened by dissolving out only a portion of said water soluble binder and is then ruptured by pulling said two layers apart, so that the dry, unsoiled two-ply facing material can be subjected to normal handling without damage to the material, and after use, the facing material and any solid waste matter deposited thereon can be immersed in water for a time, swirled around in the water to dissolve out only a portion of said water soluble binder, and pulled apart into two layers as above described, to produce a self-supporting, inner fibrous layer to be discarded separately from the outer layer, and a separate assemblage of substantially all said natural wood pulp fibers that were originally in said outer layer, which assemblage of fibers together with any residue of said solid waste matter not rinsed away by said swirling action can be flushed down a waste disposal system, where after the dissolving out of said water soluble binder is completed the assemblage will disintegrate into a multiplicity of separate individual fibers or small clumps of fibers.

2. The two-ply facing material of claim 1 in which synthetic wood pulp fibers are present at the boundary surface of said inner layer adjacent said interface in a quantity sufficient to occupy no more than about 4 percent of the area occupied by exposed fiber segments contained in said inner layer at its said boundary surface.

3. The two-ply facing material of claim 1 in which synthetic wood pulp fibers are present at the boundary surface of said inner layer adjacent said interface in a quantity sufficient to occupy no more than about 2 percent of the area occupied by exposed fiber segments contained in said inner layer at its said boundary surface.

4. The two-ply facing material of claim 1 in which said outer layer is substantially free of synthetic wood pulp fibers.

5. The two-ply facing material of claim 4 in which the concentration of synthetic wood pulp fibers in said inner layer is greatest in a region that is spaced from the external boundary surface of the inner layer adjacent said interface.

6. The two-ply facing material of claim 4 in which the boundary surface of said inner layer adjacent said interface is substantially free of synthetic wood pulp fibers.

7. The two-ply facing material of claim 1 in which said inner layer contains no more than about 20 percent by weight of synthetic wood pulp fibers.

8. The two-ply facing material of claim 1 in which said inner layer contains no more than about 10 percent by weight of synthetic wood pulp fibers.

9. The two-ply facing material of claim 1 in which said inner layer contains some textile length fibers intermixed with said natural wood pulp fibers and said synthetic wood pulp fibers.

10. The two-ply facing material of claim 1 in which said outer layer contains some textile length fibers in addition to said natural wood pulp fibers.

11. The two-ply facing material of claim 1 which is superimposed on an absorbent fibrous batt to form an absorbent product.

12. The absorbent product of claim 11 which is superimposed on and attached to a liquid impermeable backing sheet to form a disposable infant's diaper.

13. The two-ply facing material of claim 1 in which said water soluble adhesive binder is substantially less soluble in urine than in water.

14. The two-ply facing material of claim 13 in which said water soluble adhesive binder is substantially insoluble in urine.

15. In a diaper structure comprising a facing layer, an adsorbent batt and an impervious backing layer in which said facing layer and said backing sheet are outermost layers and said batt is positioned between said facing layer and said backing sheet, the improvement wherein said facing layer comprises the high loft, low density, nonwoven fibrous material of claim 1.

16. A method of producing a high loft, low density nonwoven, fibrous two-ply facing material for an absorbent product, such as a diaper, which comprises:

bringing together a first outer layer of irregularly arranged, intersecting, overlapping, mechanically interengaged, loosely assembled, natural wood pulp fibers defining interstices therebetween, and a second inner layer of similarly disposed fibers including intermixed natural wood pulp fibers and thermoplastic synthetic wood pulp fibers, said synthetic wood pulp fibers having a length and denier generally similar to natural wood pulp fibers, said second layer containing generally in the range of about 10 percent to about 30 percent by weight of thermoplastic synthetic wood pulp fibers, and said synthetic wood pulp fibers being present at the boundary surface of said second layer adjacent said first layer in a quantity sufficient to occupy no more than about 6 percent of the area occupied by the exposed fiber segments contained in said second layer at its said boundary surface, said synthetic wood pulp fibers having a melting point lower than the melting point of the other fibers in said two layers;

applying heat in the absence of pressure to said two fibrous layers thus brought together, to fuse at least some of said synthetic wood pulp fibers to each other and to some of said other fibers within said second layer to form a self-supporting fibrous structure in said second layer;

introducing a water soluble adhesive binder into said two fibrous layers and at the interface where said two layers have been brought together as described; and drying and curing said binder to produce a facing material with sufficient mechanical integrity to allow normal handling of said facing material, and in addition, help provide, together with the already existing mechanical engagement of whole fibers in said first layer, sufficient mechanical integrity in said first layer to prevent its disintegration when the bond between said two layers is ruptured to produce delamination of the two layers after only a portion of said water soluble adhesive binder has been dissolved out of the facing material and delaminating forces have been applied to the two layers.

17. The method of claim 16 in which synthetic wood pulp fibers are present at the boundary surface of said second layer that is adjacent said first layer, when the second layer is brought together with it in the first step of said method, in a quantity sufficient to occupy no more than about 4 percent of the area occupied by exposed fiber segments contained in said second layer at its said boundary surface.

18. The method of claim 16 in which synthetic wood pulp fibers are present at the boundary surface of said second layer that is adjacent said first layer, when the second layer is brought together with it in the first step of said method, in a quantity sufficient to occupy no more than about 2 percent of the area occupied by exposed fiber segments contained in said second layer at its said boundary surface.

19. The method of claim 16 in which said first layer that is brought together with said layer in the first step of said method is substantially free of synthetic wood pulp fibers.

20. The method of claim 19 in which the concentration of synthetic wood pulp fibers in said second layer is greatest in a region spaced from the boundary surface of said layer that is adjacent said first layer when the second layer is brought together with it in the first step of said method.

21. The method of claim 19 in which the boundary surface of said second layer adjacent said first layer when the two layers are brought together in the first step of said method is substantially free of synthetic wood pulp fibers.

22. The method of claim 16 in which said second inner layer that is brought together with said first layer in the first step of said method contains no more than about 20 percent by weight of synthetic wood pulp fibers.

23. The method of claim 16 in which said second layer that is brought together with said first layer in the first step of said method contains no more than about 10 percent by weight of synthetic wood pulp fibers.

24. The method of claim 16 in which said second layer that is brought together with said first layer in the first step of said method contains some textile length fibers intermixed with said natural wood pulp fibers and said synthetic wood pulp fibers.

25. The method of claim 16 in which said first layer that is brought together with said second layer in the first step of said method contains some textile length fibers in addition to said natural wood pulp fibers.

26. The method of claim 16 in which said water soluble adhesive binder is substantially less soluble in urine than in water.

27. The method of claim 26 in which said water soluble adhesive binder is substantially insoluble in urine.

* * * * *